(12) United States Patent
Miersch-Wiemers et al.

(10) Patent No.: US 7,987,839 B2
(45) Date of Patent: Aug. 2, 2011

(54) METHOD TO DETERMINE A FUEL COMPOSITION

(75) Inventors: Oliver Miersch-Wiemers, Stuttgart (DE); Georg Mallebrein, Korntal-Muenchingen (DE); Carlos Koster, Campinas (BR); Stephan Uhl, Markgroeningen (DE); Juergen Pfeiffer, Pforzheim (DE)

(73) Assignee: Robert Bosch GmbH, Stuttgart (DE)

( * ) Notice: Subject to any disclaimer, the term of this patent is extended or adjusted under 35 U.S.C. 154(b) by 708 days.

(21) Appl. No.: 12/120,009

(22) Filed: May 13, 2008

(65) Prior Publication Data

US 2008/0283030 A1    Nov. 20, 2008

(30) Foreign Application Priority Data

May 14, 2007   (DE) .......................... 10 2007 022 592

(51) Int. Cl.
*F02D 41/00* (2006.01)

(52) U.S. Cl. .......................... 123/679; 123/1 A; 123/525

(58) Field of Classification Search ................. 123/1 A, 123/295, 300, 403, 486, 492, 494, 497, 456, 123/525, 530, 672, 679, 699; 701/101–105, 701/110, 112; 73/114.38, 118.01, 118.02; 60/274, 276, 277, 285, 286
See application file for complete search history.

(56) References Cited

U.S. PATENT DOCUMENTS

| | | | |
|---|---|---|---|
| 5,255,661 A | 10/1993 | Nankee, II et al. | |
| 7,055,311 B2 * | 6/2006 | Beutel et al. | 60/285 |
| 2004/0210378 A1 * | 10/2004 | Ellmer | 701/114 |
| 2006/0016440 A1 * | 1/2006 | Labbe | 123/673 |
| 2007/0078587 A1 * | 4/2007 | Beer et al. | 701/109 |
| 2007/0234710 A1 * | 10/2007 | Franz | 60/295 |
| 2008/0022987 A1 * | 1/2008 | Cianciara et al. | 123/696 |
| 2008/0105031 A1 * | 5/2008 | Arlt et al. | 73/23.32 |
| 2008/0120017 A1 * | 5/2008 | Rodatz et al. | 701/108 |
| 2009/0223499 A1 * | 9/2009 | Rosel | 123/672 |

FOREIGN PATENT DOCUMENTS

EP    1 118 757    7/2001

* cited by examiner

*Primary Examiner* — John T Kwon
*Assistant Examiner* — Johnny H Hoang
(74) *Attorney, Agent, or Firm* — Merchant & Gould P.C.

(57) ABSTRACT

The invention concerns a method to determine the composition of a fuel from the components ethanol and gasoline of an internal combustion engine, wherein the fuel is supplied to the internal combustion engine by a fuel supply unit and via two fuel distributor rails; and the exhaust gas is discharged from the internal combustion engine by two exhaust gas manifolds of a first and a second exhaust gas system, which are separated from each other, wherein the first and second exhaust gas system have in each case at least one exhaust gas probe and wherein current changes in the ethanol content of the fuel are evaluated from the signal differences of lambda signals from the exhaust gas probes. With this method, a change in the ethanol content of the fuel can be detected, and an explicit condition for a change in fuel can be derived. Moreover, with the method, errors in the fuel-mixture can be distinguished from an altered fuel composition, which takes place after the tank has been filled fueling.

11 Claims, 2 Drawing Sheets

METHOD TO DETERMINE A FUEL COMPOSITION

TECHNICAL FIELD

The invention concerns a method to determine the composition of a fuel from the components ethanol and gasoline of an internal combustion engine, wherein the fuel is supplied to the internal combustion engine by means of a fuel supply unit and via two fuel distributor rails; and the exhaust gas is discharged from the internal combustion engine by means of two exhaust gas manifolds of a first and a second exhaust gas system, which are separated from each other, wherein the first and second exhaust gas system have in each case at least one exhaust gas probe.

BACKGROUND

Present-day internal combustion engines according to the principle of the gasoline engine are operated as a rule with a fuel extracted from crude oil and containing hydrocarbons such as regular or premium gasoline. Alternatively alcohol fuels extracted from plants, for example from sugar cane, such as ethanol are also increasingly being used.

A motor vehicle, which takes both kinds of fuel, is referred to as a vehicle capable of adapting to the fuel, or also as a "flexible fuel vehicle", or in short as a "flex-fuel vehicle" (FFV) or as a flex-power vehicle. These types of vehicles can be operated with pure gasoline as well as with various similar fuels like, for example, ethanol, bioethanol or methanol-gas mixtures. Pure ethanol is denoted as E100-fuel. Pure gasoline is on the other hand denoted as E0-fuel. Any arbitrary mixture with xx % ethanol is denoted as Exx. In Europe, Brazil and the USA, typical fuels containing ethanol comprise approximately 75 to 85% ethanol (E75, respectively E85). The remaining 15 to 25% is gasoline.

Because ethanol has a significantly smaller stoichiometric ratio during combustion when compared with gasoline (9.0 instead of 14.7), an increased injected fuel quantity is required in a stoichiometric engine operation with ethanol. This is made more complicated by the fact that arbitrary mixtures can occur in the fuel tank as a result of the fuels put in the tank. Information about a past fueling of the tank must at the latest be present when after filling the tank, new fuel with other characteristics has arrived at the fuel distributor rail, the so-called fuel rail, respectively at the fuel-delivery control system of the internal combustion engine. An exact knowledge of the ethanol content of the fuel significantly improves the drivability of the vehicle as well as the cold starting capability and the degree of efficiency achieved by the adjustment of the parameters of the engine management system.

The engine management system of the flex-fuel vehicle must therefore adjust the engine mode of operation, especially the fuel injection mode of operation, respectively the fuel injection characteristic diagrams and the ignition characteristic diagrams, to the corresponding fuel-mixture ratio. Detection with certainty of the fuel-mixture ratio existing in the tank is required for this purpose. In so doing, it is assumed that the mixture ratio can only then change in the tank if a quantity of fuel has been added. For this reason a leading role is assigned to the fueling detection in a flex-fuel system.

State of the art is a detection, which detects the fuel level change in a vehicle at rest (fuel tank sender, signal at terminal 15). Fueling when the motor is running is not detected. The disadvantage thereby is that the fuel level measured in a vehicle at rest depends very greatly on the degree to which the vehicle is slanted. An improved fueling detection is described in a parallel application of the applicant (female).

In current flex-fuel systems the isolation of map-based pilot control errors of the fuel-mixture control, which result, for example, from variances in the dispersions of the fuel injection valves or leakages in the intake manifold, and the use of fuel containing ethanol represent large challenges. As a result of insufficient discrimination, the possibility exists that the fuel-mixture errors are mistakenly subscribed to the proportion of ethanol in the fuel or the reverse is true.

It is therefore the task of the invention to provide a method, which allows changes in the ethanol content of the fuel to be distinguished from map-based pilot control errors during the fuel-mixture preparation.

SUMMARY

The task is thereby solved, in that current changes of the ethanol content in the fuel are evaluated from signal differences in the lambda signals of the exhaust gas probes. With this method a change in the ethanol content of the fuel can be detected and an explicit condition for a change in fuel can be derived. Moreover, with this method fuel-mixture errors can be distinguished from an altered fuel composition resulting from the tank having been filled (fueling). This allows for a system to be made available, which conforms to the law in market areas where there are strict legal standards with regard to emissions and diagnostic fuel analyses, for example in Europe and the USA.

In so doing, provision is made for the elapsed time differences in the changes of the lambda signals of both exhaust gas systems to be evaluated while taking into account the differences in the lengths of the supply lines between the fuel supply unit and both of the fuel distributor rails. The change in fuel can thereby be detected with certainty when the tank is filled with a fuel with an altered content of ethanol. It is particularly advantageous if a point in time is determined, when the fuel with altered characteristics arrives at both of the fuel distributor rails. The determination of this point in time is done as a function of the volume of the fuel lines from the fuel supply unit to both of the fuel distributor rails while taking into account the current engine operating points of the internal combustion engine, as, for example, engine rotational speed, relative load—respectively cylinder filling.

It is particularly advantageous if the evaluation of the lambda signals is started after the input of a fueling signal from a separate fueling detection. In a preferred variation, the fueling detection as well as the increase in fill level can be evaluated both when the motor vehicle is at rest as well as when it is moving. This is the case as it is described in a parallel application of the applicant (female).

It is advantageous in the method if the differences in lengths of the supply lines between the fuel supply unit and both of the fuel distributor rails can be varied by design-engineering measures. In so doing, the difference in length and consequently the differences in volume can stand in relation to the current consumption in such a way that a significant, temporal separation of the lambda signals thereby results; and for this reason an optimal assessment of the signals can be assured.

Provision is made in a preferred variation of the method for a condition for a change in fuel to be derived from the evaluation of the signal differences in the lambda signals and/or for the magnitude of the change in the ethanol content of the fuel to be determined, which, for example, can result from the comparison of the lambda signals with, for example, threshold values, which are a function of the engine operating points. According to the order of magnitude of the signal differences and their temporal occurrence, a change in fuel can then be detected, and an analogous signal can be affixed to it; or the ethanol content of the fuel can be suggested from the size of the signal changes. It is also additionally possible that an existing fuel-mixture error can be detected with this information, if, for example, the occurrence of the signal changes of the lambda signals and their signal size do not conform to the signal paradigm for a change in fuel. It is furthermore advantageously possible to use the signal paradigms coming from the exhaust gas probes for diagnostic purposes. This could be done, for example, to detect an errant operation of an exhaust gas probe or to assess the functional capability of the fuel supply system.

If after determining the change in the ethanol content of the fuel, new adaptation values for a closed-loop lambda control are determined and stored, the altered stoichiometry of the new fuel resulting from the fuel-mixture generation can thus accordingly be taken into account. In this way, the fuel injection mode of operation, respectively the fuel injection characteristic diagrams, can be adapted to the new fuel-mixture ratio. Thus, an optimal closed-loop lambda control is also possible when altered fuel characteristics exist.

Before the evaluation of the lambda signals of both of the exhaust gas systems occurs, provision is made in a preferred variation of the method for a balancing to be implemented in both of the fuel distributor rails of the internal combustion engine when the fuel composition is constant and homogeneous or when the fuel supply is error free. A standardization of the lambda signals, which are specific to their respective exhaust gas manifold, can thus result for the compensation of tolerances and/or errors during the fuel-mixture generation in, for example, the fuel injection valves. This standardized value can then be stored as a non-volatile adaptation value and is consequently made available to the closed-loop lambda control.

If a balancing is implemented at a steady state operating point of the internal combustion engine, for example when the engine is idling, before the evaluation procedure of the lambda signals, the advantage results in that no dynamic changes disturb the balancing action. This is especially the case when the internal combustion engine is idling.

Provision is made in a preferred application for the method to be employed with the previously described variations in internal combustion engines, which can be operated with a fuel whose ethanol content varies, as is the case in the flex-fuel vehicle (FFV) and in those vehicles which have an intake manifold fuel injection or a direct gasoline injection.

BRIEF DESCRIPTION OF THE DRAWINGS

The invention is described in detail below using the examples of embodiment depicted in the figures. The following are shown.

DETAILED DESCRIPTION

Figure 1:
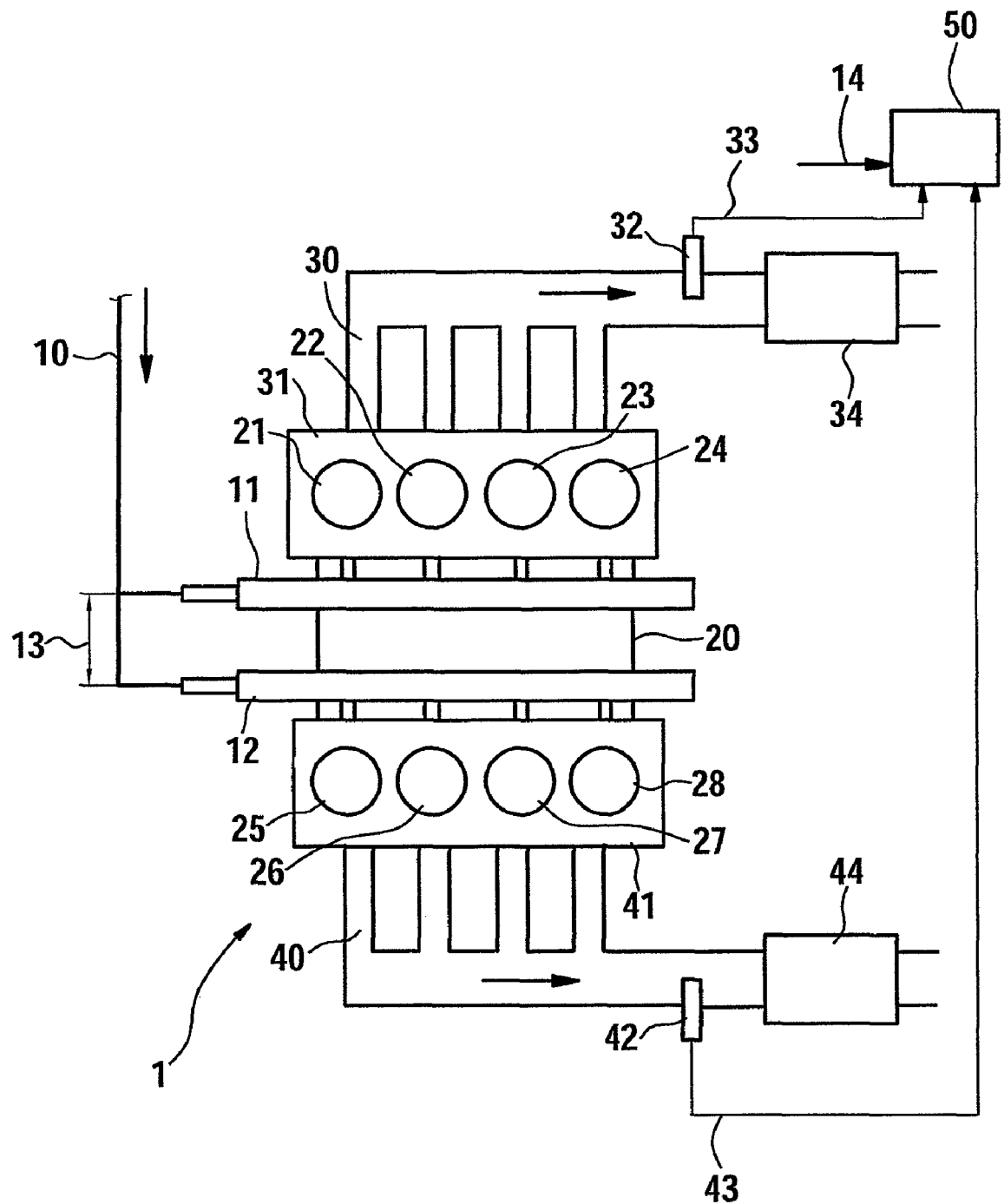
FIG. 1 is an internal combustion engine as the technical environment of the method according to the invention.

FIG. 1 schematically depicts the technical environment, wherein the method according to the invention is applied. An internal combustion engine 1 is depicted, which has an engine block 20, which has in the example shown eight cylinders 21 through 28, whereby the exhaust gas of the first four cylinders 21 through 24 is collected in a first exhaust gas system 30 with a first exhaust gas manifold 31 and is discharged into an exhaust gas aftertreatment system. The exhaust gas of the cylinders five to eight 25 through 28 is collected in a second exhaust gas system 40 with a second exhaust gas manifold 41 and is fed to the exhaust gas aftertreatment system. This is the precondition for the application of the method according to the invention. This is generally speaking the case for V-engines but also applies to in-line engines with 6 cylinders.

It is prevalent, as can be seen in FIG. 1, for provision to be made for at least one catalytic converter 34, 44 to serve as the exhaust gas aftertreatment system respectively in each of the two exhaust gas systems 30, 40. In front of said catalytic converters in the direction of flow of the exhaust gas in the exhaust gas duct, at least one exhaust gas probe 32, 42 is in each case disposed, with which a lambda value can be determined. As an output signal of both of the exhaust gas probes 32, 42, the first exhaust gas probe 32 delivers a first lambda signal 33 and the second exhaust gas probe 42 a second lambda signal 43. Both lambda signals 33, 43 from both of the exhaust gas manifolds 31, 41 are provided to a plotting unit 50. Additionally a fueling signal 14 can be applied to the input side of the plotting unit 50, which is transmitted from an unspecified fueling detection.

The fuel supply of the internal combustion engine 1 results by means of a fuel supply unit 10 (for example a fuel pump), which supplies the fuel to two separate fuel distributor rails 11, 12 (fuel rail); whereby the first fuel distributor rail 11 supplies the first four cylinders 21 through 24 with fuel, and the second fuel distributor rail 12 supplies the cylinders five to eight 25 through 28 with fuel. It is characteristic in the depicted internal combustion engine 1 for the fuel supply lines between the fuel supply unit 10 and the fuel distributor rails 11, 12—and consequently the fuel injection valves—to have a difference in length. The fuel supply lines are laid out as "returnless" in the application of the method according to the invention, i.e. the fuel distributor rails 11, 12 have no return line to the fuel tank.

If a filling of the tank (fueling) now occurs with a fuel other than that contained in the tank, the fuel with the altered characteristics will initially reach the first fuel distributor rail 11 and consequently the first four cylinders 21 through 24 and subsequently the second fuel distributor rail 12 and consequently the cylinders five to eight 25 through 28 in a time period, which is dependent on the volume of the fuel supply lines to the first fuel distributor rail 11 and to the second fuel distributor rail 12 as well as on the operating point of the internal combustion engine. Provision is made in a preferred embodiment for the difference in length 13 to be variably designed by means of design-engineering measures, wherein the difference in length 13 and consequently the volumetric differences should stand in relation to the current consumption in such a way that a significant temporal separation results from that.

When the fuel with the altered characteristics arrives, which depending on its composition possesses another stoichiometry, another lambda value initially locally arises in the first exhaust gas manifold 31. A change in the lambda value then arises in the second exhaust gas manifold 41 with a time delay. This time delay can then, for example, be evaluated in the plotting unit 50.

Figure 2:
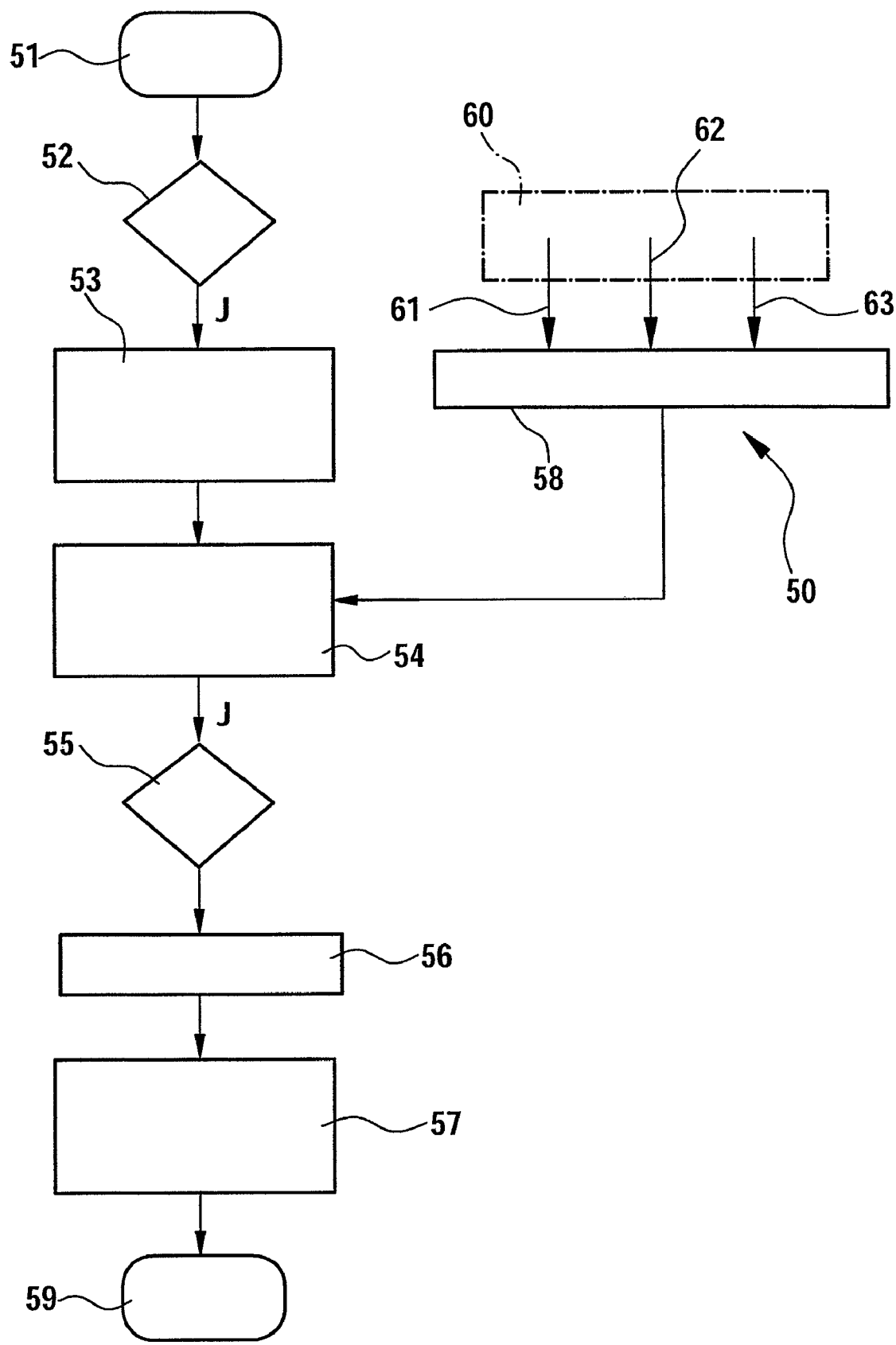
FIG. 2 is a flow diagram of the method, which is schematically depicted.

FIG. 2 shows a flow diagram of the method according to the invention as a component part of the plotting unit 50.

The functionality according to the invention concerns a non-continuous operating process. The activation first occurs after a start 51 if a fueling of the motor vehicle has been determined with a fueling query 52. If this is the case, the evaluation system is activated in such a way that a change in the fuel composition situated in the fuel tank of the motor vehicle has if need be taken place. The point in time, when the fuel, with which the tank was just filled, arrives, for example, at the fuel injection valves is determined in a calculation unit 53 by means of integration of the quantity of fuel injected as a function of the volume of the fuel line up to the first fuel distributor rail 11 and up to the second fuel distributor rail 12 while taking into account the currently active engine operating points as a function of the engine rotational speed and the relative load, respectively the cylinder filling.

In the following, an evaluation of the lambda signals 33, 43 of both of the exhaust gas probes 32, 42 within the first and second exhaust gas manifold 31, 41 takes place in a lambda signal plotting unit 54 at the time when the altered fuel is expected to arrive at the fuel injection valves. Previously a standardization of the lambda signals 33, 43 specific to the respective exhaust gas manifold was implemented in a standardization unit 58 and stored as a non-volatile adaptation value.

In order to generate these standardized values, a constant fuel-mixture ratio 63 in the fuel tank as well as an error free fuel supply 61 is assumed. In addition it can be advantageous to use a steady state operating point 62 as a reference for the standardization. The idle of the internal combustion engine can, for example, be used for this purpose.

As soon as the lambda signals 33, 43 of the exhaust gas manifolds 31, 41 exceed a determinable threshold in chronological order as a function of the difference in length 13 of the fuel supply lines, which results by means of a lambda signal query 55, the system detects a fueling with a fuel having altered characteristics. If this is the case, a state condition for a detected "altered fuel in the system" is affixed. In so doing, the firing order of the cylinders and the direction, in which new fuel flows through the system, must be taken into account.

As soon as the condition "altered fuel in the system" is present, a fixing of the adaptation values of the closed-loop lambda control occurs in a succeeding calculation and storage unit 57. The changes in the stoichiometry during the fuel-mixture generation, which are now emerging, are stored as a new ethanol value in the system and are used for the adaptation of the quantity of fuel injected and the ignition timing.

The evaluation procedure then initially moves to the end 59 and can be restarted when a new fueling signal 14 occurs.

The method described can be implemented as a software and/or a hardware solution and can at least be a part of the overriding engine management system. The method can be employed in engines with intake manifold fuel injection (SRE) as well as in engines with direct gasoline injection (BDE).

The invention claimed is:

1. A method of determining a fuel composition having at least components of ethanol and gasoline, in that the fuel is supplied to an internal combustion engine via a fuel supply unit and a plurality of fuel distributor rails, wherein an exhaust gas is discharged from the internal combustion engine via a first exhaust manifold of a first exhaust system and a second exhaust manifold of a second exhaust system, wherein the first and second exhaust systems are separated from each other, the method comprising:
   providing an at least a first lambda signal from an at least one exhaust gas probe disposed in the first exhaust system;
   providing an at least a second lambda signal from an at least one exhaust gas probe disposed in the second exhaust system; and
   evaluating an ethanol content of the fuel based on a real time change in a difference in the first lambda signal and the second lambda signal.

2. A method according to claim 1, further comprising evaluating an elapsed time difference in a real time change of the first lambda signal and the second lambda signal, wherein differences in a supply line length between the fuel supply unit and the plurality of fuel distributor rails are considered in the elapsed time difference evaluation.

3. A method according to claim 1, further comprising determining a first point in time in that a fuel with altered characteristics arrives at the plurality of fuel distributor rails, wherein the first point in time is a function of a volume of a plurality of fuel supply lines leading from the fuel supply unit up to the plurality of fuel distributor rails and one or more currently active engine operating points of the internal combustion engine.

4. A method according to claim 1, wherein evaluating includes evaluating after an input of a fueling signal from a separate fueling detection.

5. A method according to claim 2, further comprising varying differences in a supply line length between the fuel supply unit and the plurality of fuel distributor rails by means of a design engineering measure.

6. A method according to claim 1, further comprising deriving a condition for a change in fuel from an evaluation of a difference in the first lambda signal and second lambda signal or determined from a magnitude of a change in an ethanol content of the fuel.

7. A method according to claim 6, further comprising storing at least one newly ascertained adaptation value for a closed-loop lambda control after the determination of the change in the ethanol content.

8. A method according to claim 1, further comprising balancing the plurality of the fuel distributor rails when the fuel composition is constant and homogeneous or then the supply unit is error free, wherein the balancing occurs before an evaluation of a difference in the first lambda signal and the second lambda signal.

9. A method according to claim 8, wherein balancing is implemented during a steady state operating point of the internal combustion engine.

10. A method according to claim 9, wherein balancing is implemented when the internal combustion engine is in an idling operating state.

11. A method of using an internal combustion engine having and an intake manifold fuel injection or a direct gasoline injection, wherein the internal combustion engine is operated with a fuel with a changing ethanol content, for the implementation of a method for determining an ethanol and a gasoline content of a fuel, in that the fuel is supplied to an internal combustion engine via a fuel supply unit and a plurality of fuel distributor rails, wherein an exhaust gas is discharged from the internal combustion engine via a first exhaust manifold of a first exhaust system and a second exhaust manifold of a second exhaust system, wherein the first and second exhaust system are separated from each other, the method comprising: providing an at least first lambda signal from an at least one exhaust gas probe disposed in the first exhaust system; providing an at least a second lambda signal from an at least one exhaust gas probe disposed in the second exhaust system; and evaluating an ethanol content of the fuel based on a real time change in a difference in the first lambda signal and the lambda signal.

* * * * *